(12) United States Patent
Smith, Jr. et al.

(10) Patent No.: US 6,774,275 B2
(45) Date of Patent: Aug. 10, 2004

(54) PULSE FLOW REACTION

(75) Inventors: Lawrence A. Smith, Jr., Houston, TX (US); William M. Cross, Jr., Seabrook, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 178 days.

(21) Appl. No.: 10/223,192

(22) Filed: Aug. 19, 2002

(65) Prior Publication Data

US 2004/0069683 A1 Apr. 15, 2004

Related U.S. Application Data (60) Provisional application No. 60/313,987, filed on Aug. 21, 2001, provisional application No. 60/323,227, filed on Sep. 19, 2001, and provisional application No. 60/334,560, filed on Nov. 30, 2001.

(51) Int. Cl.[7] .............................................. C07C 2/62
(52) U.S. Cl. ...................... 585/731; 585/730; 585/953
(58) Field of Search ................................ 585/731, 730, 585/953

(56) References Cited

U.S. PATENT DOCUMENTS

| | | | |
|---|---|---|---|
| 4,288,640 A | 9/1981 | Schuster et al. | 568/855 |
| 5,081,321 A | 1/1992 | Fukuhara et al. | 568/881 |
| 5,799,877 A | 9/1998 | Gupta et al. | 239/8 |
| 6,331,657 B1 | 12/2001 | Kaizik et al. | 568/882 |
| 6,407,295 B1 | 6/2002 | Kaizik et al. | 568/883 |

OTHER PUBLICATIONS

T.S.Chou, F.L.Worley, Jr. and D. Luss, Transition to Pulsed Flow in Mixed–Phase Cocurrent Downflow through a Fixed Bed., Ind. Eng. Chem., Process Des. Dev., vol. 16, No. 3, 1977, p. 424–427.

J.R.Blok, J. Varkevisser and A.A.H. Drinkenburg, Transition to Pulsing Flow, Holdup and Pressure Drop in Packed Columns with Cocurrent Gas–Liquid Downflow, Chemical Engineering Science, vol. 38, No. 5 pp. 687, 1983.

G.Christensen, S.J. McGovern, S. Sundaresan, Cocurrent Downflow of Air and Water in a Two–Dimensional Packed Column, AIChE Journal, vol. 32, No. 10, Oct. 1986, pp. 1677–1689.

Jaco. G. Boelhouwer, Nonsteady operation of trickle–bed reactors: hydrodynamics, mass and heat transfer, chapter 2, pp. 23–52, Nov. 28, 2001.

*Primary Examiner*—Thuan D Dang
(74) *Attorney, Agent, or Firm*—Kenneth H. Johnson (57) ABSTRACT

A method of operating a multi-phase downflow reactor so as to induce a pulsing flow regime is disclosed. The pulse may be induced by increasing the gas rate while maintaining the liquid rate until a pressure drop sufficient to induce the pulse flow is achieved. The method is particularly useful in the sulfuric acid catalyzed alkylation of olefins in a reactor packed with a stainless steel/polypropylene mesh.

10 Claims, 4 Drawing Sheets

PULSE FLOW REACTION

This application claims the benefit of provisional application 60/313,987 filed Aug. 21, 2001, provisional application 60/323,227 filed Sep. 19, 2001, and provisional application 60/334,560 filed Nov. 30, 2001.

BACKGROUND OF THE INVENTION

1. Field of the Invention

The present invention relates to multi-phase reactions where a hydraulic regime is utilized, which provides pulsations, to yield greater mixing and associated interfacial mass transfer and heat transfer. By obtaining a desired vapor and liquid mass flux in a down flow reactor process, fluid pulsations can be induced.

2. Related Information

The pulse flow regime has been studied in regard to trickle-bed reactors. Generally, trickle-bed reactor refers to a solid particulate pack bed down flow reactor operating in the trickle flow or gas continuous regime. A hydraulic map called a Baker plot is often used to indicate the mass fluxes required to obtain a given hydraulic regime (i.e., Trickle, pulse, bubble flow). Weekman, V. W., Jr., and J. E. Myers, "Fluid-Flow characteristics of concurrent gas-liquid flow in packed beds", AIChE Journal, 10, 951 (1964), provides a map of the various hydraulic regimes found in packed beds. These pulses yield turbulent mixing within the reactor system and provide a higher level of mass and heat transfer, not typical of commercial reactors which tend to operate in the hydraulic region known as trickle flow.

Pulse flow in a mixed phase reactor is defined as a hydraulic region in which waves of liquid continuous slugs of material move down the reactor. In between each wave is a region of flow which is considered to be gas continuous. The pulses are discrete bands of material with higher overall density than that of the material both in front and behind the pulse or wave. By changing the overall liquid and vapor mass fluxes within this hydraulic region, the frequency at which the pulses flow down the reactor can be manipulated. Higher overall mass flux, yields higher frequency pulses, and lower mass flux yield lower frequency pulses. The mechanism for development of this type of flow is not due to oscillations provided by some type of mechanical device, rather it is a known two phase (vapor/liquid) hydraulic region which is a function of the relative vapor and liquid velocities.

Figure 1:
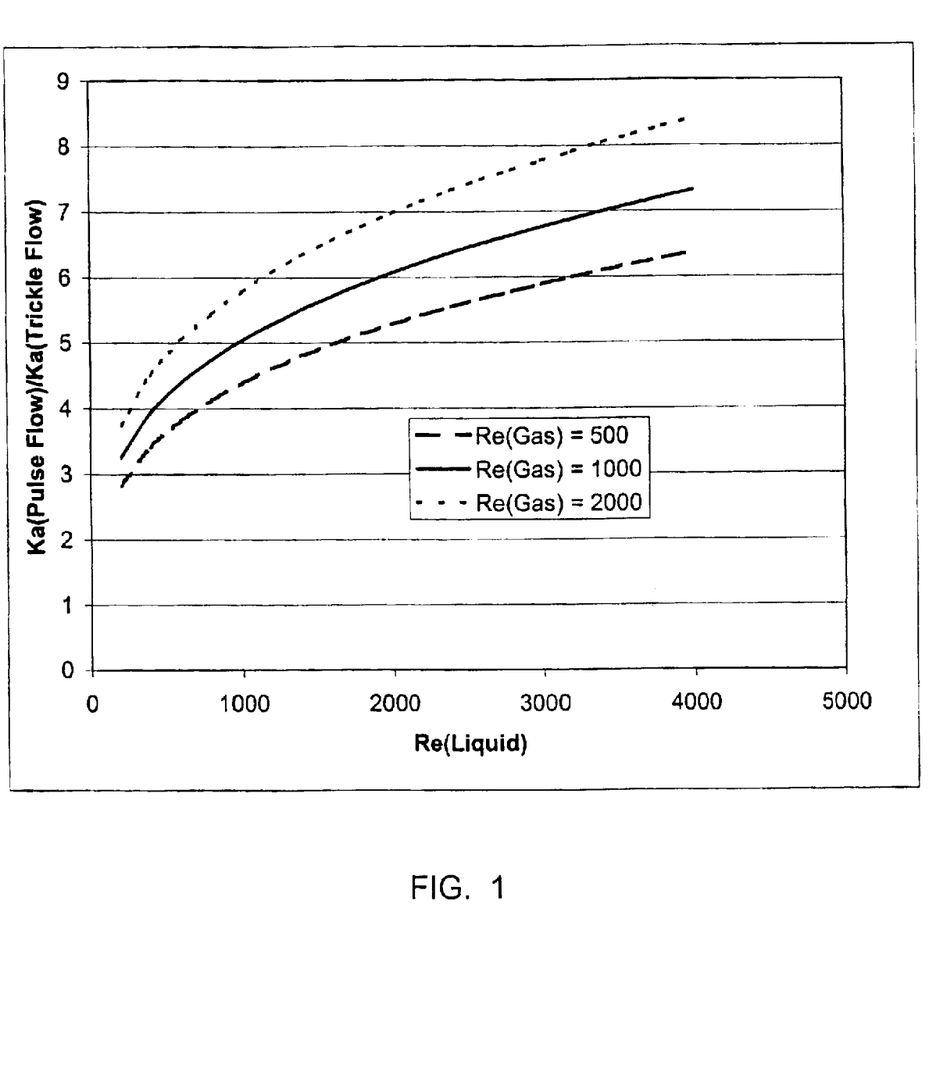
FIG. 1 is a comparison in graphical form of the mass transfer coefficients in pulse flow and trickle flow.

Fukushima, S. and Kusaka, K., *J. of Chem. Eng. Japan* 10, p. 468 (1977) provided Equations 1 and 2, which demonstrate the increase in mass transfer as one moves into the pulse flow regime. The difference between the liquid to gas mass transfer coefficient for trickle flow and pulsing flow can be seen from the following two equations where equation (1) is for trickle flow and equation (2) is for pulsing flow:

$$k_L a_i = 2.05 {S_p}^{0.2} Re_l^{0.73} Re_G^{0.2} Sc^{0.5} (dp/D)^{0.2} (1-h_{ext}) D_{ml}/dp^2 \quad (1)$$

$$k_L a_i = 0.11 Re_l Re_G^{0.4} Sc^{0.5} (dp/D)^{-0.3} (1-h_{ext}) D_{ml}/dp^2 \quad (2)$$

where:

$k_L$ is the mass transfer coefficient
$a_i$ is the specific interfacial surface area
$S_p$ is the external surface of particle divided by the square of the particle diameter
$Re_l$ is the modified Reynolds number of the liquid (density removed)
$Re_G$ is the modified Reynolds number of the gas (density removed)
Sc is Schmidt number (ratio of the momentum diffusivity to the mass diffusivity
dp is the particle diameter,
D is the diameter of the reactor,
$h_{ext}$ is the liquid hold up (ratio of the volume of liquid held up in the reactor over the total reactor volume), and
$D_{ml}$ is the molecular diffusivity of the gas This is presented graphically in FIG. 1 where the ratio of pulse flow mass transfer coefficient to trickle bed mass transfer coefficient is shown to increase with the Reynolds number of the liquid or gas. The Reynolds number of either the liquid or gas is directly proportional to the flow rate, all other variables (diameter of reactor, density and viscosity of component) being constant.

Schuster et al U.S. Pat. No. 4,288,640 identifies a narrow region within the Baker plot where heat transfer benefit occurs as one increases the mass fluxes of the gas and liquid and approaches pulse flow. This region of operation is called transitional flow. Transitional flow represents a narrow region of mass fluxes between trickle flow and pulse flow. This region is essentially on the transition line of the flow map separating pulse flow from trickle flow, which lies at a point where a small change in liquid flow causes a relatively large change in differential pressure drop across the bed. Schuster et. al list a range of $\Delta P/L$ of twice the $\Delta P/L$ obtained during trickle bed operation and characterizes the pulse region as one where fluctuations in the pressure difference across the reactor occur and the pressure fluctuations as having the same frequency as the pulses. It is known, however, that the pulse regime extends far beyond the differential pressure drop change of twice trickle flow.

A plot of gas vs. liquid mass flux for pilot and commercial scale reactors was presented in "Trickle Bed Reactors", Charles Satterfield, AIChE Journal, Vol. 21, No. 2, March 1975, pp. 209–228. The author observed that the operating region for the pilot scale reactors was in trickle regime; whereas, some commercial reactors operated in the pulse region. This suggests that during scale-up to commercial size some commercial reactors were inadvertently designed to operate in the pulse region, since at the time, running in pulse mode was considered to lead to undesirable hydraulic instability and breakup of catalyst particles in the packed bed.

With typical trickle bed reactors, like those used for hydrotreating using a solid catalyst, the main resistance towards the desired hydrogenation include: 1) mass transfer from the gas phase into the liquid phase, 2) mass transfer from the liquid phase onto and off of the catalyst surface, 3) diffusion into and out of the catalyst pore space, 4) adsorption of the reactants onto the catalyst surface, 5) chemical reaction, and 6) desorption of the products into the pore space.

Although reactor operation in the pulse flow region may provide interesting mass transfer benefits, two main concerns exist. The first addresses fixed bed catalyst life. Due to the high liquid and vapor rates, vibration of the fixed bed may occur causing physical catalyst degradation and abrasion over time. Secondly a problem in scale up from pilot plant units may be encountered. The small size of pilot plant reactors induces wall effects which occlude space for radial pulse dispersion and it is not known whether larger diameter reactors provide an equivalent flow pattern at the same liquid and vapor velocities. It is an advantage of this invention that a multi-phase co-current flow reactor system that operates efficiently in the pulse flow region is provided.

SUMMARY OF THE INVENTION

Briefly the present invention is the operation a multiphase downflow reactor under conditions of liquid and vapor flow and the packing to induce a pulse flow regime. The process is preferably carried out in a vertically disposed reactor containing a contact structure having a void space of greater than 50 volume %. The packing system may be comprised of materials that are either inert or catalytically active in nature.

DESCRIPTION OF THE PREFERRED EMBODIMENTS

Pulse flow is obtained at high gas and liquid flow rates. The pulses are characterized by large mass and heat transfer rates. Increased catalyst wetting and a continuous mixing between parallel flowing rivulets diminish flow maldistribution. In addition, the formation of local hot spots is reduced, leading to an intrinsically safer process and diminished catalyst deactivation. The pulses continuously mobilize the stagnant liquid holdup to the point where its stagnant nature disappears. Since stagnant holdup represents about 10 to 30 percent of the total liquid holdup in trickle flow operations, its more dynamic character during pulsing flow enhances reactor performance. Axial dispersion is considerably less compared to trickle flow, due to effective radial mixing between the different parallel flowing liquid streams and disappearance of stagnant liquid hold up. Especially undesired consecutive reactions are reduced to lower levels due to better overall plug flow behavior. A further advantage of pulsing flow is much higher radial conductivity. In some cases, depending on the pulse frequency, significant changes in both yield and selectivity occur.

The main benefit with pulse regime reactor operation is that of increased mass transfer and heat transfer due to the associated turbulence produced. When the catalyst physical characteristics are optimized and the reaction kinetics are not limiting, increasing mass transfer is a key to increasing the process performance.

Some example reactions that can be conducted in the multi-phase pulsed flow reactor include:

1.) Vapor/Liquid/Liquid systems in which the packing is inert and one of the liquid phases is the catalyst for the reaction. An example is olefin/paraffin alkylation using sulfuric acid or HF as catalyst.

2.) Vapor/Liquid systems in which the packing is an inert structure that functions as a container for solid particulate catalyst, as a support for catalytic materials deposited on the surface of the structure, or is comprised of materials that are not inert and have catalytic properties. An example is hydrodesulfurization of hydrocarbon feed stocks over a supported Co—Mo catalyst.

3.) Vapor/Liquid/Solid systems in which the packing is inert. Finely divided catalyst is the solid phase dispersed in the liquid phase. An example is synthesis of methanol from $CO/H_2$. The liquid phase is an inert hydrocarbon oil containing finely divided methanol synthesis catalyst.

The pulse may be induced by increasing the gas rate while maintaining the liquid rate until a pressure drop sufficient to induce the pulse flow is achieved. Further the pulsing may be dampened while keeping the mixing characteristics by utilizing a second liquid of different viscosity. The dampening reduces the wear and tear on catalysts and also maintains more even flow rates.

The disperser comprises at least 50 volume % open space up to about 99 volume % open space. Dispersers are position within the reaction zone in the reactor. Thus, for example, the multi filament component and the structural element, e.g., knit wire, should comprise about 3 volume % to about 50 volume % of the total disperser, the remainder being open space. Such packings may be composed of metals, ceramics, plastics, and/or composite materials. Some of these materials include: Carbon steel, 304 SS, 304 L SS, 316 SS, 316 L SS, Alloy 20, Monel, Inconel, PVC, PTFE, Titanium, Nickel, Hastelloy, aluminum, other alloys, polypropylene, polyethylene, Kynar, and Teflon. A list of packings containing desirable void fractions include:

(1) Random or dumped distillation packings which are catalytically inert Dumped packings contain higher void fraction and maintain a relatively large surface area, such as, Berl Saddles (Ceramic), Raschig Rings (Ceramic), Raschig Rings (Steel), Pall rings (Metal), Pall rings (Plastic—polypropylene), Intalox® saddles, Hy-pak™, K-PAC™, Ballast-plus™, CMR®, Chempak™, Levapak®, Nutter Rings™, HcPp™, FLEXIMAX™, Hiflow®, Jaeger Tri-packs®, NOR PAC®, Intalox® Snowflake™, LANPAC™, and IMPAC™.

(2) Random or dumped distillation packings which are catalytically active. Random packings which contain at least one catalytically active ingredient. Such ingredients could include elements such as Ag, Rh, Pd, Ni, Cr, Cu, Zn, Pt, Tu, Ru, Co, Ti, Au, Mo, V, and Fe as well as impregnated components such a metal-chelate complexes, acids such as phosphoric acid, or bonded, inorganic, powdered materials with catalytic activity.

Other available dumped packings would include catalytic materials in the form of small wires which are bent and formed into various geometrical shapes such as cubes, cylinders, spheres.

(3) Structured packings which are catalytically inert. These packings are typically constructed of corrugated metal bent at various angles, wire mesh which is crimped, or grids which are horizontally stacked one on top of the other, such as GOODLOE®, MONTZ A™, and MONTZ B™ and the device of U.S. Pat. No. 6,000,685 which is incorporated herein in its entirety, which discloses contact structures comprising a plurality of sheets of wire mesh formed into vee shaped corrugations having flats between the vees, said plurality of sheets being of substantially uniform size having the peaks oriented in the same direction and substantially in alignment, said sheets being separated by a plurality of rigid members oriented normally to and said resting upon said vees.

(4) Structured catalytic distillation packings which are intended to hold particulate catalysts, or structured distillation packings composed of a catalytically active material. Structures similar in form to the structured distillation packings or rolled bales which contain pockets can be used to contain particulate catalysts. These are commercially know as catalytic distillation packings, such as packing composed of flexible, semi-rigid open mesh tubular elements which contain particulate catalyst(s) (U.S. Pat. No. 5,431,890). Other suitable structures are disclosed in U.S. Pat. No. 5,730,843 which is incorporated herein in its entirety and which discloses structures that have a rigid frame made of two substantially vertical duplicate grids spaced apart and held rigid by a plurality of substantially horizontal rigid members and a plurality of substantially horizontal wire mesh tubes mounted to the grids to form a plurality of fluid pathways among the tubes, said tubes being empty or containing catalytic or non catalytic materials.

In particular the pulse flow is utilized in the sulfuric acid alkylation process wherein an olefin is reacted with an iso-alkane in the presence of sulfuric acid using an internal static mixing system comprising the combination of a vertical reactor having a reaction zone and the disperser disposed in said reaction zone, particularly for carrying out paraffin alkylation using an acid catalyst. A preferred disperser comprises mesh wire with a multi filament component or expanded metal intertwined with a multi filament component, said multi filament selected from inert polymers, catalytic polymers, catalytic metals or mixtures thereof. The wire mesh provides the structural integrity of the system as well as the open space required in reactors for the movement of vapors and liquids though the system. The disperser may be comprised of sheets, bundles or bales of the co-knit wire and the multi filament component. The system may also comprise the co-knit wire and multi filaments within a frame. The reaction zone may comprise the entire column or a portion thereof. The present dispersers achieve radial dispersion of the fluid or fluidized materials in the reactor.

(5) Demisters and Co-knit structures which are catalytically inert or active. Demisters and co-knit structures are typically used for liquid-liquid coalescers and coalescing of mists. They are known as "mist eliminators" or demisters and are composed of one or more materials which are knit together to form a mesh. The stitched mesh is then crimped, stretched, and folded or bundled to provide the desired amount of surface area per volume ratio.

Several demister and coalescer materials such as those constructed by Amistco Separation Products, Inc. of Alvin, Tex. are composed of single materials or co-knit metal wires and multi-filaments of polypropylene, Teflon, PVDF, or polyester. Information used to describe these filaments include: a) the filament count, and b) the denier of the filaments. Other acceptable demisters include perforated sheets and expanded metals, open flow cross channel structures which are co-woven.

Additionally, catalytic materials can be woven or interwoven into structures such as sulfonated vinyl rein (e.g. Amberlyst) and catalytic metals such as Ag, Rh, Pd, Ni, Cr, Cu, Zn, Pt, Tu, Ru, Co, Ti, Au, Mo, V, and Fe. There may be up to 100 or more multi filaments intertwined with the knitted wire or expanded metal. The catalytic metal filaments are generally of higher denier because of their greater density.

(6) Monoliths which are catalytically inert or active. Monoliths are structures containing multiple, independent, vertical channels and may be constructed of various materials such as plastic, ceramic, or metals. The channels are typically square; however, other geometries could be utilized. The segmented channels could be constructed, impregnated, or coated with active catalytic materials.

A preferred disperser comprises a conventional liquid-liquid coalescer of a type which is operative for coalescing vaporized liquids. These are commonly known as "mist eliminators" or "demisters", however, in the present invention the element functions to disperse the fluid materials in the reactor for better contact. A suitable disperser comprises a mesh such as a co-knit wire and fiberglass mesh. For example, it has been found that a 90 needle tubular co-knit mesh of wire and multi filament fiberglass such as manufactured by ACS Industries LLC of Houston, Tex., can be effectively utilized, however, it will be understood that various other materials such as co-knit wire and multi filament Teflon (Dupont™), steel wool, polypropylene, PVDF, polyester or various other co-knit materials can also be effectively utilized in the apparatus. Various wire screen type packings may be employed where the screens are woven rather than knitted. Other acceptable dispersers include perforated sheets and expanded metals, open flow cross channel structures which are co-woven with fiberglass or other materials such as polymers co-knit with the wire mesh expanded or perforated sheets. Various wire screen type packings may be employed where the screens are woven rather than knitted. Thus, preferably the multi filament component and the structural element, e.g., knit wire, should comprise about 35 volume % to 80 volume % of the total disperser.

In a preferred embodiment the reactor is packed with a special disperser comprising a wire mesh packing material containing 0.011 SS306 turned wire and interwoven 800 denier polypropylene. One source of the material is Amistco Separation Products, Inc. of Alvin, Tex. The packing is useful for contacting alkylation reactants, i.e., olefins and alkanes, and the liquid sulfuric acid catalyst. Packing density for this material is approximately 7 lbs/ft.$^3$ which provides a surface area of 444 ft.$^2$ for five feet of the material in a four inch diameter glass column. Surface area relating to the walls only of the column is 5.23 ft$^2$. The alkylation reactor is packed with a wire mesh packing material containing 0.011 SS306 turned wire and interwoven 800 denier polypropylene. A pressure drop of at least about 0.06 psi/ft of packing has been shown sufficient to produce pulse flow for this packing.

Other suitable dispersers are disclosed in U.S. Pat. No. 5,730,843 which is incorporated herein in its entirety and which discloses structures that have a rigid frame made of two substantially vertical duplicate grids spaced apart and held rigid by a plurality of substantially horizontal rigid members and a plurality of substantially horizontal wire mesh tubes mounted to the grids to form a plurality of fluid pathways among the tubes, said tubes being empty or containing catalytic or non catalytic materials and U.S. Pat. No. 6,000,685 which is incorporated herein in its entirety and which discloses contact structures comprising a plurality of sheets of wire mesh formed into vee shaped corrugations having flats between the vees, said plurality of sheets being of substantially uniform size having the peaks oriented in the same direction and substantially in alignment, said sheets being separated by a plurality of rigid members oriented normally to and said resting upon said vees.

The changes in holdup and pressure for the packing were determined for a three phase trickle bed reactor using a model system to simulate the sulfuric acid alkylation of butene with isobutane. Sulfolane was used to simulate the acid (heavy liquid, HL), normal hexane to simulate the liquid hydrocarbon (light liquid, LL) and nitrogen to simulate the gaseous hydrocarbon feed (gas, g). Measurements were made for 1) liquid holdup and 2) pressure drop across the packed column containing five feet of the packing as described. In the data below four main sets of conditions were measured including: 1) Boundary, 2) Base Case, 3) High LL Case, and 4) High HL Case. Herein HL stand for heavy.

Figure 2:
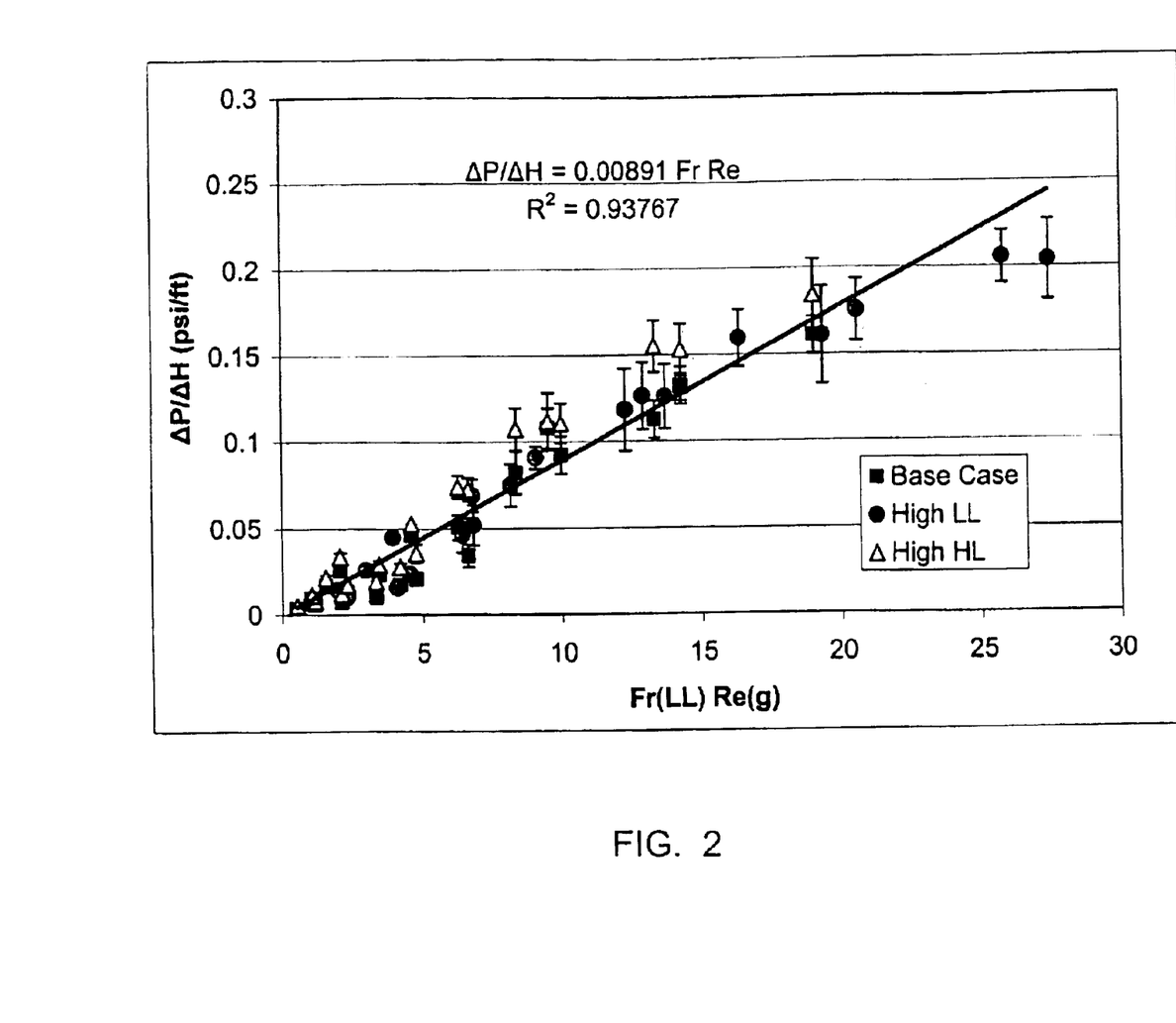
FIG. 2 is a plot of differential pressure versus the product of the Froude Number of the light liquid and the Reynolds Number of the vapor in a packed reactor.

FIG. 2 depicts graphically the effect of flow rates on the pressure drop. The pressure drop in pounds per square inch per foot of column is plotted as a function of the product of the Froude Number of the hexane, Fr(LL), and the Reynolds Number of the nitrogen, RE(g). The Froude Number is the superficial velocity of the fluid (in this case the hexane) divided by the square root of the product of the gravity constant times the diameter of the reactor. The error bars for given values are a result of the data being taken in the pulse flow regime. As shown, all of the points beyond a Fr(LL) Re(g)=5 are in the pulse regime. This equates to approximately a 0.06 psi/ft pressure drop provided by the packing which induces the pulse flow.

Figure 3:
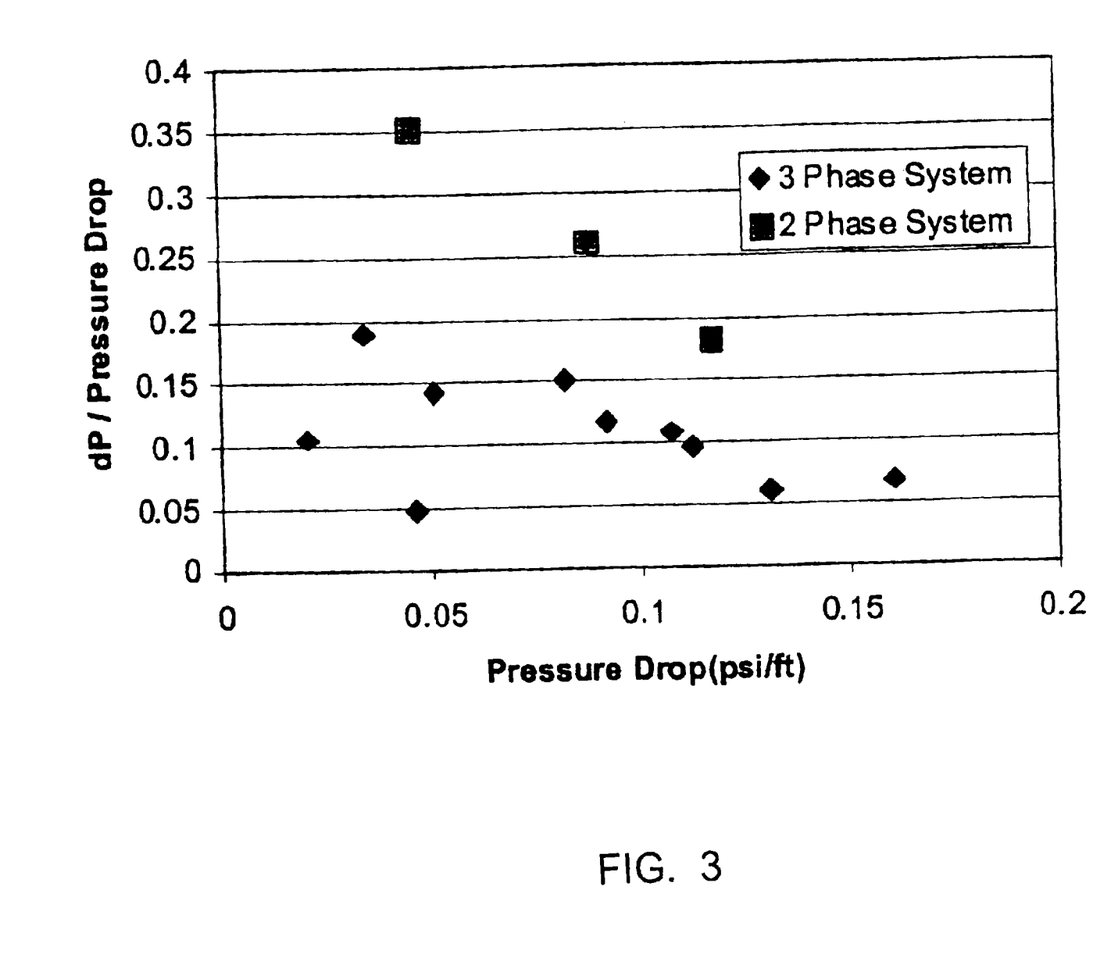
FIG. 3 is a plot of the ratio of the pressure deviations caused by pulse flow to the overall pressure drop versus the overall pressure drop when a three phase (gas/liquid/liquid) system is used.

A unique feature of using a three phase (vapor/liquid/liquid) system is that mass fluxes can be adjusted whereby only one liquid phase is essentially operating in the pulse regime. With higher viscosity fluids (such as sulfolane or sulfuric acid) it was found that in order to obtain pulse flow at a fixed gas flux, the liquid mass flux would have to be increased when compared to a lower viscosity fluid (such as hexane or iso-butane). When the liquids of different viscosity are used it was found that there was a controlling fluid which forced pulsing (i.e. the lower viscosity fluid). Combination of a low viscosity fluid and a high viscosity fluid allows for operation where one liquid is essentially operating in pulse flow and the other in trickle. This type of operation is useful because it provides the good mixing associated with pulse flow but limits the pressure swings caused by the pulses due to dampening by the second viscous liquid phase. This is graphically depicted in FIG. 3 wherein the ratio of the pressure deviation to the overall pressure drop is plotted against the overall pressure drop.

The present pulse system is useful in a process for the alkylation of isoparaffin with olefin or olefin precursor comprising contacting a fluid system comprising acid catalyst, isoalkane and olefin in concurrent flow, preferably downflow into contact in a reaction zone with present system under conditions of temperature and pressure to react said isoparaffin and said olefin to produce an alkylate product. Preferably, the fluid system comprises a liquid and is maintained at about its boiling point in the reaction zone. The olefin precursor is an oligomer of one or more tertiary olefins such as the dimer, trimer, etc. of isobutene or a material which corresponds to said oligomer.

The reaction of oligomer of tertiary olefins with isoalkanes is on a molar basis with the constituent tertiary olefins of the oligomer rather than the oligomers. The alkylate product corresponds to the reaction of the tertiary olefin and isoalkanes.

For the purpose of illustration and not a limitation of the process, it is believed that instead of the expected reaction between the oligomer and the isoalkane, the oligomer is cracked into its olefin components which react with the isoalkane on a molar basis:

1) diisobutene+2 isobutane→2 isooctane (2,2,4-trimethyl pentane)
2) triisobutene+3 isobutane→3 isooctane (2,2,4-trimethyl pentane)

The conventional view had been that the product of 1) would be a $C_{12}$ alkane and the product of 2) would be a $C_{16}$ alkane whereas the product of reactions 1) and 2) is the same and is indistinguishable from a conventional cold acid alkylation product of the reaction:

3) 2 butene-2+2 isobutane→2 isooctane
4) 3 butene-2+3 isobutane→3 isooctane

The great advantage of the present invention is that although acid alkylations are extremely exothermic and require substantial refrigeration to maintain the reaction temperature in optimum range to prevent side reactions, the present reaction of the oligomers with the isoalkane to produce the alkylate in the same yields required less refrigeration making the process less expensive for the same yield of useful product.

One particular method of producing oligomer is that carried out in a catalytic distillation, for example, units formerly used to produce MTBE can readily be converted to producing oligomer merely by changing the feed to the reactor since the same catalyst serves both reactions.

Preferably, the oligomer comprises $C_8$ to $C_{16}$ olefins corresponding to oligomer prepared from $C_3$ to $C_5$ olefin. In a preferred embodiment the oligomer has 6 to 16 carbon atoms and corresponds to oligomers which are prepared from $C_4$ to $C_5$ olefins.

The widest use of the paraffin alkylation is for the preparation of a $C_8$ gasoline component. The feed to this process is usually normal butene and tertiary butane contained in a "cold acid" reaction usually with sulfuric acid or HF. The normal butene (butene-2, for example) is a component of light naphtha along with normal butane, isobutane and tertiary butene. The separation of the normal butene from the isobutene can be effected by fractionation with difficulty because of their close boiling point. A preferred way to separate these olefin isomers or those of the $C_5$ analogs is to react the more reactive tertiary olefin to form a heavier product which is easily separated from the normal olefins by fractionation.

Heretofore, the tertiary olefin was reacted with a lower alcohol, such as methanol or ethanol, to form ethers, such as methyl tertiary butyl ether (MTBE), ethyl tertiary butyl ether (ETBE), tertiary amyl methyl ether (TAME) which have been used as gasoline octane improvers but are being phased out because of health concerns.

The oligomerization of the tertiary olefin is also a preferred reaction when carried out on a naphtha stream with the separation of normal olefin being easily achieved by fractionation from the heavier (higher boiling) oligomers (mainly dimer and trimer). The oligomers may be used as gasoline components but there are limits to the amount of olefin material desirable or allowed in gasoline and it is frequently necessary to hydrogenate the oligomers for use in gasoline. The most desirable component for gasoline blending is $C_8$, e.g., isoctane (2,2,4 trimethyl pentane).

The oligomer may be cracked back to the original tertiary olefins and used in cold acid reaction. However, the present invention has found that it is not necessary to crack the oligomer which may constitute the olefin feed to cold acid reaction with the alkane or may be co-fed with mono olefins. As noted above the result is the same product as the mono olefin alone with the additional benefit of a less exothermic overall reaction requiring less refrigeration and, hence, a lower energy cost for the alkylation.

The oligomerization process produces a heat of reaction that does not require the magnitude of heat removal as in the cold acid process. In fact, when the oligomerization is carried out in a catalytic distillation type reaction, the heat of reaction is removed as boilup, which in this type of reaction is the lower boiling mono olefins and alkanes which are being separated from the oligomer. Thus, even though there is heat produced in the oligomerization it is of no cost to the production of the gasoline since it is used in the fractionation, and the operating cost of the alkylation unit is reduced by the use of oligomer to replace some or all of the conventional short chain olefin.

In a preferred embodiment of the present alkylation process, a light naphtha stream comprising normal and tertiary olefins is contacted with an acid resin catalyst under oligomerization conditions to preferentially react a portion of the tertiary olefins with themselves to form oligomers, and feeding said oligomers to an alkylation zone with an isoalkane in the presence of an acid alkylation catalyst to produce an alkylation product comprising the alkylate of said tertiary olefin and said isoalkane.

The oligomerization may be carried out in a partial liquid phase in the presence of an acid cation resin catalyst either in straight pass type reaction or in a catalytic distillation reaction where there is both a vapor and liquid phase and a concurrent reaction/fractionation. Preferably, the feed is a $C_4$–$C_5$, $C_4$ or $C_5$ light naphtha cut. The tertiary olefins may include isobutene, and isoamylenes and are more reactive than the normal olefin isomers and are preferentially oligomerized. The primary oligomer products are dimers and trimers. The isoalkanes preferably comprise isobutane, isopentane or mixtures thereof.

When a straight pass reactor is used, such as that disclosed in U.S. Pat. Nos. 4,313,016; 4,540,839; 5,003,124; and 6,335,473, the entire effluent comprising the oligomer, normal olefins and isoalkanes may be fed to an acid alkylation reaction. The normal alkanes are inert under the conditions of the present alkylation. Under alkylation conditions the isoalkane reacts with the normal olefin to form alkylate product and with the individual constituent olefins of the oligomers to form the alkylate product. The implication of the result of the present process is that the oligomers are dissociated or in some manner make their constituent olefins available for reaction with isoalkanes. Thus, the reaction will produce:

1) isobutene oligomer+isobutane→isooctane;
2) isobutene oligomer+isopentane→branched $C_9$ alkanes;
3) isoamylene oligomer+isobutane→branched $C_9$ alkanes;
4) isoamylene oligomer+isopentane→branched $C_{10}$ alkanes;

whereas it would have been expected that reaction 1) would produce at least or mostly $C_{12}$ alkanes, reaction 2) would produce at least or mostly $C_{13}$ alkanes, reaction 3) would produce at least or mostly $C_{14}$ alkanes, and reaction 4) would produce at least or mostly $C_{15}$ alkanes.

When a catalytic distillation reaction such as that disclosed in U.S. Pat. Nos. 4,242,530 or 4,375,576 is employed for the oligomerization, the oligomer is separated from the lower boiling normal olefins and alkanes in the reaction product by concurrent fractionation. The streams, normal olefins and alkanes (overheads) and oligomers (bottoms), may be united or individually fed to the alkylation or may be used individually with at least the oligomer being fed to the alkylation.

The present invention offers an improved contacting apparatus and process for producing and separating an alkylate product using sulfuric acid as catalyst. This same or similar device may also be used with other acids or acid mixtures.

The present process preferably employs a downflow reactor packed with contacting internals or packing material (which may be inert or catalytic) through which passes a concurrent multi phase mixture of sulfuric acid, hydrocarbon solvent and reactants at the boiling point of the system. The system comprises a hydrocarbon phase and an acid/hydrocarbon emulsion phase. A significant amount of sulfuric acid is held up on the packing. Reaction is believed to take place between the descending hydrocarbon phase and the sulfuric acid dispersed on the packing. Olefin continuously dissolves into the acid phase and alkylate product is continuously extracted into the hydrocarbon phase. Adjusting the pressure and hydrocarbon composition controls the boiling point temperature. The reactor is preferentially operated vapor continuous but may also be operated liquid continuous. The pressure is preferentially higher at the top of the reactor than at the bottom.

Adjusting the flow rates and the degree of vaporization controls the pressure drop across the reactor, e.g., total pressure drop across said reactor of between 0 and 4 psia. Multiple injection of olefin is preferred. The type of packing also influences the pressure drop due to the acid phase hold-up. The product mixture before fractionation is the preferred circulating solvent. The acid emulsion separates rapidly from the hydrocarbon liquid and is normally recycled with only a few minutes residence time in the bottom phase separator. Because the products are in essence rapidly extracted from the acid phase (emulsion), the reaction and/or emulsion promoters used in conventional sulfuric acid alkylation processes may be added without the usual concern for breaking the emulsion. The process may be described as hydrocarbon continuous as opposed to acid continuous.

The hydrocarbon feedstock undergoing alkylation by the method of the present invention is provided to the reaction zone in a continuous hydrocarbon phase containing effective amounts of olefinic and isoparaffinic starting materials which are sufficient for forming an alkylate product. The olefin:isoparaffin mole ratio in the total reactor feed should range from about 1:1.5 to about 1:30, and preferably from about 1:5 to about 1:15. Lower olefin:isoparaffin ratios may also be used.

The olefin component should preferably contain 2 to 16 carbon atoms and the isoparaffin component should preferably contain 4 to 12 carbon atoms. Representative examples of suitable isoparaffins include isobutane, isopentane, 3-methylhexane, 2-methylhexane, 2,3-dimethylbutane and 2,4-dimethylhexane. Representative examples of suitable olefins include butene-2, isobutylene, butene-1, propylene, pentenes, ethylene, hexene, octene, and heptene, merely to name a few and as described above may be oligomers of these olefins.

In the fluid process the system uses hydrofluoric or sulfuric acid catalysts under relatively low temperature conditions. For example, the sulfuric acid alkylation reaction is particularly sensitive to temperature with low temperatures being favored in order to minimize the side reaction of olefin polymerization. Petroleum refinery technology favors alkylation over polymerization because larger quantities of higher octane products can be produced per available light chain olefins. Acid strength in these liquid acid catalyzed alkylation processes is preferably maintained at 88 to 94% by weight using the continuous addition of fresh acid and the continuous withdrawal of spent acid. Other acids such as solid phosphoric acid may be used by supporting the catalysts within or on the packing material.

Preferably, the process of the present invention should incorporate relative amounts of acid and hydrocarbon fed to the top of the reactor in a volumetric ratio ranging from about 0.01:1 to about 2:1, and more preferably in a ratio ranging from about 0.05:1 to about 0.5:1. In the most preferred embodiment of the present invention, the ratio of acid to hydrocarbon should range from about 0.1:1 to about 0.3:1.

Additionally, the dispersion of the acid into the reaction zone should occur while maintaining the reactor vessel at a temperature ranging from about 0° F. to about 200° F., and more preferably from about 35° F. to about 130° F. Similarly, the pressure of the reactor vessel should be maintained at a level ranging from about 0.5 ATM to about 50 ATM, and more preferably from about 0.5 ATM to about 20 ATM. Most preferably, the reactor temperature should be maintained within a range from about 40° F. to about 110° F. and the reactor pressure should be maintained within a range from about 0.5 ATM to about 5 ATM.

In general, the particular operating conditions used in the process of the present invention will depend to some degree upon the specific alkylation reaction being performed. Process conditions such as temperature, pressure and space velocity as well as the molar ratio of the reactants will affect the characteristics of the resulting alkylate product and may be adjusted in accordance with parameters known to those skilled in the art.

An advantage of operating at the boiling point of the present reaction system is that there is some evaporation which aids in dissipating the heat of reaction and making the temperature of the incoming materials closer to that of the materials leaving the reactor as in an isothermal reaction.

Once the alkylation reaction has gone to completion, the reaction mixture is transferred to a suitable separation vessel where the hydrocarbon phase containing the alkylate product and any unreacted reactants is separated from the acid. Since the typical density for the hydrocarbon phase ranges from about 0.6 g/cc to about 0.8 g/cc and since densities for the acid generally fall within the ranges of about 0.9 g/cc to about 2.0 g/cc, the two phases are readily separable by conventional gravity settlers. Suitable gravitational separators include decanters. Hydrocyclones, which separate by density difference, are also suitable.

Figure 4:
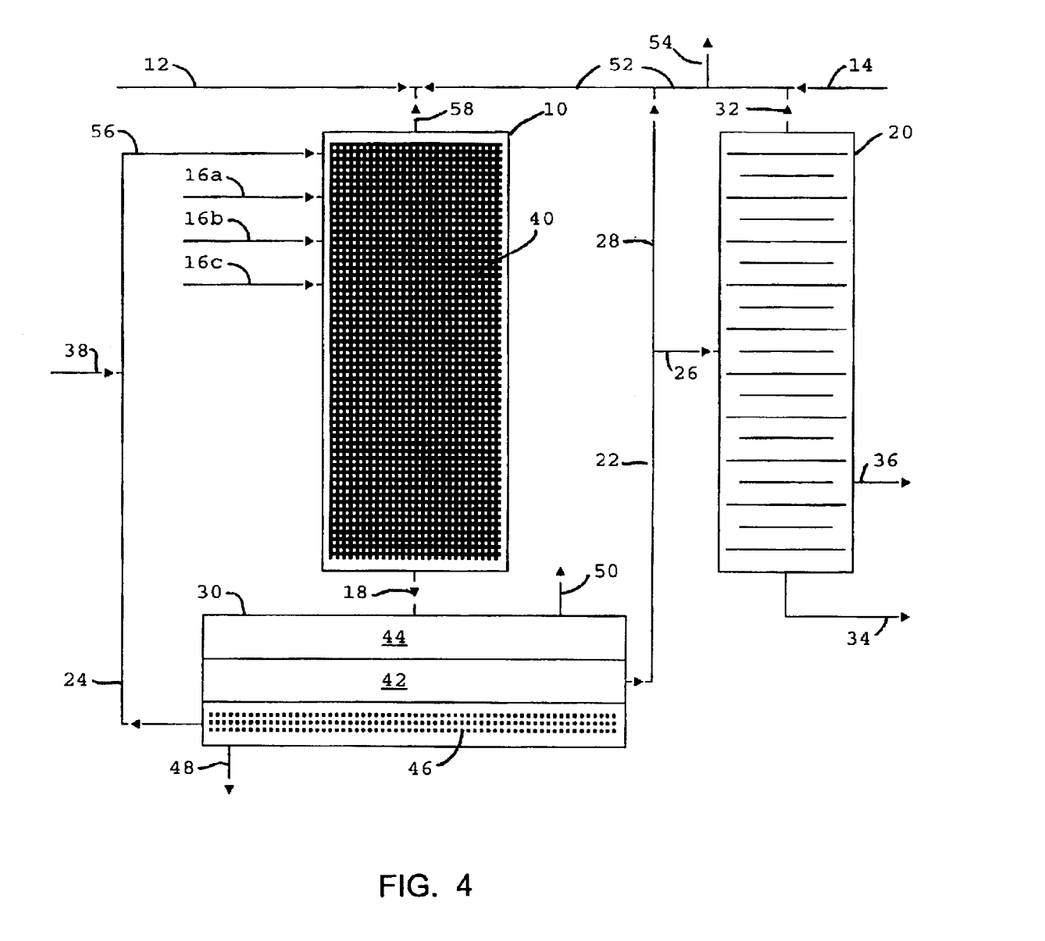
FIG. 4 is a schematic representation of the first aspect of the present apparatus in which the present alkylation process may be carried out.

One alkylation embodiment is shown in the FIG. 4 which is a simplified schematic representation of the apparatus and flow of the process. Such items as valves, reboilers, pumps, etc., have been omitted.

The reactor 10 is shown containing a disperser mesh 40. The present dispersers achieve radial dispersion of the fluid or fluidized materials in the reactor. The feed to the reactor comprises an olefin fed via line 12 such as n-butene and an isoparaffin (e.g., isobutane) fed via line 14 through line 52. Preferably a portion of the olefin is fed along the reactor via lines 16a, 16b, and 16c. A liquid acid catalyst such as $H_2SO_4$ is fed via line 56 and make-up acid may be supplied through line 38. The hydrocarbon reactants are fed to the reactor which is preferably a generally cylindrical column via line 58 and through appropriate dispersing means (not shown) into the disperser mesh 40, for example, a co-knit wire and fiberglass mesh.

The hydrocarbon reactants and non reactive hydrocarbons (e.g., normal butane) are intimately contacted with the acid catalyst as the alkylation proceeds. The reaction is exothermic. The pressure as well as the quantities of reactants are adjusted to keep the system components at the boiling point but partially in the liquid phase as the system components pass down flow through the reactor in mixed vapor\liquid phase and out through line 18 into decanter 30. In the decanter the system components are separated into an acid phase 46 containing the catalyst, a hydrocarbon phase 42 containing the alkylate, unreacted olefin and unreacted isoparaffin, and non reactive hydrocarbons and a vapor phase 44 which may contain some of each of the components and any lighter hydrocarbon components which are removed from the system via line 50 for further handling as appropriate.

Most of the acid phase is recycled via line 24 and 56 into the reactor. Make-up acid may be added via line 38 and build-up spent acid removed via line 48.

The hydrocarbon liquid phase is removed via line 22 with a portion recycled to the top of the reactor via line 28. The remainder of hydrocarbon phase is fed to distillation column 20 via line 26 where it is fractionated. Normal butane, if present in the feed, can be removed via line 36 and the alkylate product is removed via line 34. The overheads 32 are primarily unreacted isoalkane which is recycled via line 52 to the top of reactor 10.

Experimental Set Up for Alkylation of Isoparaffin+Olefin

For the following examples the laboratory reactor is 15 feet high by 1.5 inches diameter. It is packed with varying amounts and types of packing material. The $H_2SO_4$ inventory is about 1 liter depending on the holdup of the packing used. The surge reservoir is about 3 liters and passes all the acid plus liquid hydrocarbon out the bottom to circulate a two-phase mixture with a single pump. Feeds are introduced at the top of the reactor to flow down with the recycle mixture. Vapor is produced by heat of reaction plus ambient heat gains and helps force the liquids down through the packing creating great turbulence and mixing. Most of the vapors are condensed after the reactor outlet. Uncondensed vapor and liquid hydrocarbon product passes through an acid de-entrainer then through the backpressure regulator to the de-isobutanizer. Mass flow meters are used for feed flows and a Doppler meter measures the circulation rate. Liquid products from the de-isobutanizer are weighed. However, the vent flow rate is estimated as being the difference between the mass flow metered feed in and the weighed liquid products out. GC analyzes all hydrocarbon products, including the vent. Titration is used for spent acid assay.

Operation

In the following examples the experimental unit circulates hydrocarbon and acid down flow at the boiling point of the hydrocarbons present. Pressure and temperature readings are logged electronically. The reactor outlet temperature and pressure are used to calculate the amount of $iC_4$ in the recycle hydrocarbon using an $iC_4$/Alkylate flash calculation.

A backpressure regulator that passes both product liquid and vapor to the de-isobutanizer tower, maintains the pressure. A small amount of $N_2$ may be used primarily to keep acid from backing up into the feed line. However, too much $N_2$ will cause a decrease in product quality by diluting reactive isoparaffin in the vapor phase.

The circulation pump in the experimental setup circulates both the acid emulsion layer and the liquid hydrocarbon layer. Alternatively, these two phases may be pumped separately.

The acid inventory is maintained by momentarily diverting the entire recycle through a measuring tube using a three-way valve. The trapped material settles in seconds to form two layers. The volume percent acid layer and hydrocarbon layer is then used in conjunction with the Doppler meter reading to estimate the volumetric circulation rates of both phases.

The DP (pressure higher at the top or reactor inlet) is maintained between 0 and 3 psi by manipulating the circulation rates and the heat balance around the unit. Different packing usually requires different vapor and liquid flow rates to load to the same DP. Most of the time, the ambient heat gains and the heat of reaction provide adequate vapor (mostly $iC_4$) loading.

Because of refrigeration constraints, about 1–3 lbs/hr of extra liquid $iC_4$ may be introduced with the feed to provide some trim cooling. This excess $iC_4$ is relatively small and does not significantly affect the $iC_4$/Olefin ratio since the circulating hydrocarbon rates are typically on the order of 100–200 pounds per hour. It is the circulating hydrocarbon flow rate and composition that dominates the $iC_4$ ratios to everything else.

Typical Operating Conditions for C4 Alkylation in the Examples

| Feed olefin | C4's |
|---|---|
| Olefin in - lbs/hr | 0.25–.50 |
| Alky out - lbs/hr | 0.50–1.2 |
| Rxn Temp out - F. | 50–60 |
| Rxn Psig out | 6–16 |
| DP - Psi | 0.5–3.0 |
| Recycle rates: | |
| Acid phase - L/min | 0.3–1 |
| HC phase - L/min | 1–3 |
| Wt % iC4 in HC recycle | 75–45 |
| Wt % H2SO4 in Spent acid | 83–89 |
| Wt % H2O in Spent acid | 2–4 |
| Fresh acid addition - lbs/gal alky | 0.3–0.5 |
| Packing Type | 1 or 2 - see notes below |
| Packing Hgt in feet | 10–15 |
| Pack density lbs/ft3 | 5–14 |

Notes:
1. Packing type 1 is .011 inch diameter 304 ss wire coknitted with 400 denier multi-filament fiberglass thread every other stitch.
2. Packing type 2 is .011 inch diameter alloy 20 wire coknitted with 800 denier multi-filament poly propylene yarn every other stitch.

EXAMPLE 1

| Refinery C4 Olefins used as feedstocks | | |
|---|---|---|
| To the Lab Unit: | Low iB | 38% iB in total olefins |
| methane | 0.02 | 0.00 |
| ethane | 0.00 | 0.00 |
| ethene | 0.00 | 0.00 |
| propane | 0.77 | 0.41 |
| propene | 0.14 | 0.16 |
| propyne | 0.02 | 0.00 |
| propadiene | 0.01 | 0.02 |
| iso-butane | 23.91 | 47.50 |
| iso-butene | 0.90 | 15.90 |
| 1-butene | 20.02 | 10.49 |
| 1,3-butadiene | 0.02 | 0.19 |
| n-butane | 22.63 | 10.79 |
| t-2-butene | 18.05 | 7.93 |
| 2,2-dm propane | 0.09 | 0.00 |
| 1-butyne | 0.00 | 0.01 |
| m-cyclopropane | 0.03 | 0.03 |
| c-2-butene | 12.09 | 5.43 |
| 1,2-butadiene | 0.00 | 0.01 |
| 3M-1-butene | 0.26 | 0.04 |
| iso-pentane | 0.98 | 0.02 |
| 1-pentene | 0.06 | 0.82 |
| 2M-1-butene | 0.01 | 0.01 |
| n-pentane | 0.01 | 0.03 |
| t-2-pentene | 0.00 | 0.08 |
| c-2-pentene | 0.00 | 0.00 |
| t-3-pentadiene | 0.00 | 0.08 |
| c-1,3-pentadiene | 0.00 | 0.00 |
| unknowns | 0.01 | 0.08 |
| | 100.00 | 100.00 |

Comparison of Refinery produced Alkylate with Lab Unit results using similar low iB C4 feed

| | Plant A | Plant B | Lab 1 | Lab 2 |
|---|---|---|---|---|
| iC5 | 6.27 | 2.70 | 2.51 | 2.78 |
| 2,3-dmb | 4.05 | 2.84 | 2.80 | 3.02 |
| C6 | 1.63 | 1.19 | 1.00 | 1.15 |
| 2,2,3-tmb | 0.20 | 0.17 | 0.18 | 0.19 |
| C7 | 7.17 | 5.55 | 4.35 | 4.35 |
| TM C8 | 53.88 | 61.76 | 66.84 | 66.93 |
| DM C8 | 12.27 | 12.47 | 12.69 | 12.44 |
| TM C9 | 5.04 | 4.22 | 2.89 | 2.74 |
| DM C9 | 0.57 | 1.01 | 0.29 | 0.18 |
| TM C10 | 1.14 | 0.91 | 0.70 | 0.64 |
| UNK C10 | 0.51 | 0.54 | 0.29 | 0.29 |
| TM C11 | 0.99 | 0.77 | 0.69 | 0.71 |
| UNK C11 | 1.09 | 0.02 | 0.00 | 0.00 |
| C12 | 4.37 | 1.71 | 4.72 | 4.60 |
| C13 | 0.00 | 1.58 | 0.00 | 0.00 |
| C14 | 0.03 | 1.57 | 0.05 | 0.00 |
| C15 | 0.00 | 0.13 | 0.00 | 0.00 |
| HV'S | 0.05 | 0.04 | 0.00 | 0.00 |
| UNK | 0.74 | 0.83 | 0.00 | 0.00 |
| sum | 100.00 | 100.00 | 100.00 | 100.00 |
| Av MW | 113.4 | 116.0 | 114.9 | 114.6 |
| Bromine no. | <1 | <1 | <1 | <1 |
| Total Sulfur ppm | <10 | <10 | <10 | <10 |
| TOTAL % TM | 61.05 | 67.66 | 71.12 | 71.01 |
| TM C8/DM C8 (ratio) | 4.39 | 4.95 | 5.27 | 5.38 |
| TM C9/DM C9 (ratio) | 8.85 | 4.19 | 10.08 | 15.57 |

Typical vent analysis:

| | wt % |
|---|---|
| hydrogen | 0.000 |
| oxygen | 0.124 |
| nitrogen | 3.877 |
| methane | 0.019 |
| carbon monoxide | 0.000 |
| carbon dioxide | 0.000 |
| ethane | 0.000 |
| ethene | 0.000 |
| ethyne | 0.000 |
| propane | 1.066 |
| propene | 0.000 |
| propadiene | 0.000 |
| iso-butane | 81.233 |
| iso-butene | 0.021 |
| 1-butene | 0.000 |
| 1,3-butadiene | 0.031 |
| n-butane | 3.398 |
| t-2-butene | 0.000 |
| m-cyclopropane | 0.000 |
| c-2-butene | 0.000 |
| iso-pentane | 0.968 |
| 1-pentene | 0.000 |
| n-pentane | 0.000 |
| C5 + | 0.391 |

EXAMPLE 2

Effect of Isobutylene (iB) on Alky Quality

| | 100% iB | 38% iB | lab 1 low iB |
|---|---|---|---|
| iC5 | 3.66 | 3.97 | 2.78 |
| 2,3-dmb | 3.60 | 3.56 | 3.02 |
| C6 | 1.42 | 0.52 | 1.15 |
| 2,2,3-tmb | 0.40 | 0.23 | 0.19 |
| C7 | 5.27 | 5.08 | 4.35 |

-continued

Effect of Isobutylene (iB) on Alky Quality

|  | 100% iB | 38% iB | lab 1 low iB |
|---|---|---|---|
| TM C8 | 50.79 | 56.95 | 66.93 |
| DM C8 | 11.77 | 12.64 | 12.44 |
| TM C9 | 6.07 | 4.22 | 2.74 |
| DM C9 | 0.58 | 0.45 | 0.18 |
| TM C10 | 2.06 | 1.33 | 0.64 |
| UNK C10 | 1.14 | 0.67 | 0.29 |
| TM C11 | 2.54 | 1.28 | 0.71 |
| UNK C11 | 1.00 | 0.00 | 0.00 |
| C12 | 8.30 | 8.99 | 4.60 |
| C13 | 0.07 | 0.00 | 0.00 |
| C14 | 0.28 | 0.14 | 0.00 |
| C15 | 0.12 | 0.00 | 0.00 |
| HV'S | 0.38 | 0.00 | 0.00 |
| UNK | 0.54 | 0.00 | 0.00 |
| sum | 100.00 | 100.00 | 100.00 |
| Av MW | 119.1 | 117.3 | 114.9 |
| Bromine no. | ~1 | <1 | <1 |
| Total Sulfur ppm | <10 | <10 | <10 |
| TOTAL % TM | 61.46 | 63.77 | 71.12 |
| TM C8/DM C8 | 4.31 | 4.51 | 5.27 |
| TM C9/DM C9 | 10.51 | 9.34 | 10.08 |

EXAMPLE 3

Propylene + iC4 Alkylation

| Sample Point | product |
|---|---|
| propane | 0.01 |
| iso-butane | 9.25 |
| n-butane | 0.32 |
| iso-pentane | 0.97 |
| n-pentane | 0.00 |
| 2,3-dm butane | 2.07 |
| 2M-pentane | 0.30 |
| 3M-pentane | 0.14 |
| n-hexane | 0.00 |
| 2,4-dm pentane | 15.59 |
| 2,2,3-tm butane | 0.04 |
| 3,3-dm pentane | 0.01 |
| cyclohexane | 0.00 |
| 2M-hexane | 0.34 |
| 2,3-dm pentane | 48.97 |
| 1,1-dm cyclopentane | 0.00 |
| 3M-hexane | 0.35 |
| 2,2,4-tm pentane | 3.42 |
| n-heptane | 0.00 |
| 2,5-dm hexane | 0.37 |
| 2,4-dm hexane | 0.56 |
| 2,3,4-tm pentane | 1.52 |
| 2,3,3-tm pentane | 1.21 |
| 2,3-dm hexane | 0.64 |
| 2,2,5-tm hexane | 0.68 |
| 2,3,4-tm hexane | 0.13 |
| 2,2-dm heptane | 0.01 |
| 2,4-dm heptane | 0.03 |
| 2,6-dm heptane | 0.03 |
| 2,2,4-tm-heptane | 1.83 |
| 3,3,5-tm-heptane | 1.70 |
| 2,3,6-tm-heptane | 1.16 |
| 2,3,5-tm-heptane | 0.16 |
| tm-heptane | 1.00 |
| 2,2,6-trimethyloctane | 2.32 |
| C8s | 0.20 |
| C9s | 0.20 |
| C10s | 0.98 |
| C11s | 1.62 |
| C12s | 1.73 |
| C13s | 0.09 |

-continued

Propylene + iC4 Alkylation

| Sample Point | product |
|---|---|
| C14s | 0.05 |
| C15s | 0.01 |
| unknowns | 0.01 |
| heavies | 0.00 |
|  | 100.00 |

EXAMPLE 4

Isobutane + pentene 1 alkylation product

|  | Wt % |
|---|---|
| C5 | 5.03 |
| 2,3-dmb | 0.74 |
| C6 | 0.35 |
| DM C7 | 1.14 |
| C7 | 0.17 |
| TM C8 | 22.26 |
| DM C8 | 3.70 |
| TM C9 | 52.40 |
| DM C9 | 6.72 |
| TM C10 | 1.51 |
| UNK C10 | 0.56 |
| TM C11 | 0.16 |
| UNK C11 | 0.38 |
| C12 | 3.68 |
| C13 | 0.33 |
| C14 | 0.11 |
| C15 | 0.08 |
| HV'S | 0.03 |
| UNK | 0.63 |
|  | 100.00 |
| Avg MW | 123.2 |
| expected MW | 128 |
| feed olefin #/hr | 0.25 |
| Alky product #/hr | 0.47 |

EXAMPLE 5

Oligomerization product from C4 feedstock with 38% iB in total olefins. (This product was in turn used as the olefin feed to the lab Alkylation unit)

| iso-butane | 48.8 |
|---|---|
| iso-butene + 1-butene | 1.6 |
| n-butane | 11.2 |
| t-2-butene | 14.3 |
| c-2-butene | 6.5 |
| iso-pentane | 1.0 |
| t-2-pentene | 0.1 |
| unknowns | 1.5 |
| 2,4,4-tm-1-pentene | 4.7 |
| 2,4,4-tm-2-pentene | 1.3 |
| other C8's | 3.4 |
| grouped C12's | 4.4 |
| grouped C16's | 1.2 |
|  | 100.0 |

Oligomerization effect on Alky products using C4 feed with iB = 38% of Olefins

|  | before | after |
|---|---|---|
| iC5 | 3.97 | 2.39 |
| 2,3-dmb | 3.56 | 2.87 |

-continued

|  | | |
|---|---|---|
| C6 | 0.52 | 1.17 |
| 2,2,3-tmb | 0.23 | 0.20 |
| C7 | 5.08 | 4.95 |
| TM C8 | 56.95 | 58.34 |
| DM C8 | 12.64 | 12.80 |
| TM C9 | 4.22 | 4.15 |
| DM C9 | 0.45 | 0.35 |
| TM C10 | 1.33 | 1.29 |
| UNK C10 | 0.67 | 0.57 |
| TM C11 | 1.28 | 1.41 |
| UNK C11 | 0.00 | 0.00 |
| C12 | 8.99 | 9.41 |
| C13 | 0.00 | 0.00 |
| C14 | 0.14 | 0.11 |
| C15 | 0.00 | 0.00 |
| HV'S | 0.00 | 0.00 |
| UNK | 0.00 | 0.00 |
| sum | 100.00 | 100.00 |
| Av MW | 117.3 | 118.3 |
| Bromine no. | <1 | <1 |
| Total Sulfur ppm | <10 | <10 |
| TOTAL % TM | 63.77 | 65.19 |
| TM C8/DM C8 | 4.51 | 4.56 |
| TM C9/DM C9 | 9.34 | 11.75 |
| Operating conditions: | | |
| Olefin in - lbs/hr | .25 | .25 |
| Alky out - lbs/hr | .53 | .53 |
| Rxn Temp out - F. | 52.0 | 52.2 |
| Rxn Psig out | 12.2 | 11.8 |
| DP - Psi | ~1 | ~1 |
| Recycle rates: | | |
| Acid phase-L/min | 1.0 | 1.0 |
| HC phase - L/min | 2.6 | 2.6 |
| % | 69 | 67 |
| iC4 in HC recycle | | |
| Packing Type | 2 | 2 |
| Packing Hgt in feet | 15 | 15 |
| Pack density lbs/ft3 | 7 | 7 |

EXAMPLE 6

Alkylate quality from Isobutene + Isobutane or Oligomers of iB + iC4.

|  | iB | DIB | TIB+ |
|---|---|---|---|
| IC5 | 3.66 | 3.97 | 3.41 |
| 2,3-dmb | 3.60 | 3.70 | 3.18 |
| C6 | 1.42 | 1.36 | 1.53 |
| 2,2,3-tmb | 0.40 | 0.38 | 0.27 |
| C7 | 5.27 | 4.96 | 6.39 |
| TM C8 | 50.79 | 47.93 | 38.35 |
| DM C8 | 11.77 | 8.92 | 12.91 |
| TM C9 | 6.07 | 6.60 | 10.31 |
| DM C9 | 0.58 | 0.81 | 1.10 |
| TM C10 | 2.06 | 3.09 | 3.29 |
| UNK C10 | 1.14 | 1.18 | 1.35 |
| TM C11 | 2.54 | 2.53 | 2.72 |
| UNK C11 | 1.00 | 1.79 | 0.00 |
| C12 | 8.30 | 10.51 | 14.97 |
| C13 | 0.07 | 0.31 | 0.07 |
| C14 | 0.28 | 1.47 | 0.14 |
| C15 | 0.12 | 0.29 | 0.00 |
| HV'S | 0.38 | 0.19 | 0.00 |
| UNK | 0.54 | 0.01 | 0.00 |
| Sum | 100.00 | 100.00 | 100.00 |
| Av MW | 119.1 | 122.1 | 122.9 |
| Bromine no. | ~1 | ~1 | ~1 |
| Total Sulfur ppm | <10 | <10 | <10 |
| TOTAL % TM | 61.46 | 60.15 | 54.67 |
| TM C8/DM C8 | 4.31 | 5.37 | 2.97 |
| TM C9/DM C9 | 10.51 | 8.15 | 9.37 |

-continued

Alkylate quality from Isobutene + Isobutane or Oligomers of iB + iC4.

|  | iB | DIB | TIB+ |
|---|---|---|---|
| Operating conditions: | | | |
| Feed olefin | | | |
| Olefin in - lbs/hr | 0.25 | 0.40 | 0.25 |
| Alky out - lbs/hr | 0.49 | 0.78 | 0.48 |
| Rxn Temp out - F. | 52 | 51.6 | 51.7 |
| Rxn psig out | 13 | 13.5 | 5.7 |
| DP - psi | 2.5 | 1.1 | ~1 |
| Recycle rates: | | | |
| Acid phase - L/min | 0.8 | 0.5 | 1.0 |
| HC phase - L/min | 1.8 | 1.4 | 3.0 |
| % | 73 | 76 | 45 |
| iC4 in HC recycle | | | |
| Packing Type | 1 | 1 | 2 |
| Packing Hgt in feet | 10 | 10 | 15 |
| Pack density lbs/ft3 | 6 | 6 | 7 |

EXAMPLE 7

Expected vs. actual alkylation product MW's and moles iC4 uptake with various olefins (e.g. in theory 1 mole of C6 olefin should react with 1 mole of iC4 to form a C10 alkylate; MW=142) Results indicate depolymerization generating more and lower MW olefins that combine with additional iC4.

| | Moles iC4 uptake per mole Olefin fed | | Average product MW | |
|---|---|---|---|---|
| Olefin | Expected | Actual | Expected | Actual |
| Hexene-1 | 1.0 | 1.2 | 142 | 129 |
| Octene-1 | 1.0 | 1.4 | 170 | 135 |
| Di-isobutylene | 1.0 | 1.8 | 170 | 122 |
| Tri-isobutylene+ | 1.0 | 2.6 | 226 | 123 |

EXAMPLE 8

Isobutane + pentene 1 alkylation product

|  | Wt % |
|---|---|
| IC5 | 5.03 |
| 2,3-dmb | 0.74 |
| C6 | 0.35 |
| DM C7 | 1.14 |
| C7 | 0.17 |
| TM C8 | 22.26 |
| DM C8 | 3.70 |
| TM C9 | 52.40 |
| DM C9 | 6.72 |
| TM C10 | 1.51 |
| UNK C10 | 0.56 |
| TM C11 | 0.16 |
| UNK C11 | 0.38 |
| C12 | 3.68 |
| C13 | 0.33 |
| C14 | 0.11 |
| C15 | 0.08 |
| HV'S | 0.03 |
| UNK | 0.63 |
|  | 100.00 |

Isobutane + pentene 1 alkylation product

| | Wt % |
|---|---|
| Avg MW | 123.2 |
| expected MW | 128 |
| feed olefin #/hr | 0.25 |
| Alky product #/hr | 0.47 |

The invention claimed is:

1. A method of producing alkylate in a sulfuric acid alkylation comprising feeding a hydrocarbon component consisting of an olefin, olefin precursor or mixture thereof and an isoalkane, in at least a partial gaseous state to a downflow reactor in the presence of liquid sulfuric acid fed at a constant rate and an internal static mixing system wherein the rate of feed of said olefin, olefin precursor or mixture is increased until a pressure drop sufficient to induce the pulse flow is achieved.

2. The process according to claim 1 wherein said internal static mixing system having a disperser which comprises mesh wire with a multi filament component or expanded metal intertwined with a multi filament component, said multi filament selected from the group consisting of inert polymers, catalytic polymers, catalytic metals and mixtures thereof.

3. The method according to claim 2 wherein the liquid and vapor rates are adjusted to produce a pressure drop across said reactor of at least 0.06 pounds per square inch per foot of packing.

4. The method according to claim 1 wherein said internal static mixing system comprises a packing comprising a contact structure having a void space of greater than 50 volume %.

5. The method according to claim 4 wherein said void space is up to about 99 volume % open space.

6. The method according to claim 4 wherein said contact structure is comprised of inert material.

7. The method according to claim 4 wherein said contact structure is comprised of catalytic material.

8. The method according to claim 2 wherein said reactor is packed with a wire mesh material containing stainless steel wire and interwoven with polypropylene.

9. The method according to claim 1 wherein the pressure drop across said reactor of at least 0.06 pounds per square inch per foot of packing.

10. The method according to claim 9 wherein the total pressure drop across said reactor of between 0 and 4 psia.

* * * * *